US009405036B2

(12) United States Patent
Kadayam Viswanathan et al.

(10) Patent No.: US 9,405,036 B2
(45) Date of Patent: Aug. 2, 2016

(54) MULTIPHYSICS NMR LOGGING TECHNIQUES FOR THE DETERMINATION OF IN SITU TOTAL GAS IN GAS RESERVOIRS

(71) Applicant: SCHLUMBERGER TECHNOLOGY CORPORATION, Sugar Land, TX (US)

(72) Inventors: Ravinath Kausik Kadayam Viswanathan, Somerville, MA (US); Lukasz Zielinski, Houston, TX (US); Robert L. Kleinberg, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 733 days.

(21) Appl. No.: 13/669,211

(22) Filed: Nov. 5, 2012

(65) Prior Publication Data

US 2013/0113480 A1 May 9, 2013

Related U.S. Application Data

(60) Provisional application No. 61/555,997, filed on Nov. 4, 2011.

(51) Int. Cl.
*G01V 3/00* (2006.01)
*G01V 3/32* (2006.01)
*G01N 24/08* (2006.01)

(52) U.S. Cl.
CPC .............. *G01V 3/32* (2013.01); *G01N 24/081* (2013.01)

(58) Field of Classification Search
CPC .................................................. G01L 3/32
USPC ........................................................ 324/303
See application file for complete search history.

(56) References Cited

U.S. PATENT DOCUMENTS 4,245,313 A * 1/1981 Coates ............................ 702/13
5,680,043 A * 10/1997 Hurlimann et al. ........... 324/303
6,094,048 A * 7/2000 Vinegar et al. ................ 324/303
6,242,912 B1 * 6/2001 Prammer et al. .............. 324/303
6,859,032 B2 2/2005 Heaton et al.
7,755,354 B2 7/2010 Akkurt
2002/0167314 A1 * 11/2002 Prammer ....................... 324/303
2003/0094946 A1 * 5/2003 Galford et al. ................ 324/303
2004/0008027 A1 * 1/2004 Prammer ....................... 324/303
2004/0032257 A1 * 2/2004 Freedman ..................... 324/303
2011/0054795 A1 * 3/2011 Klein et al. ........................ 702/7
2011/0133859 A1 6/2011 Khelif et al.

FOREIGN PATENT DOCUMENTS

WO    2011133859    10/2011
WO    2013023011    2/2013

OTHER PUBLICATIONS

Cipolla et al., "IPTC 14677: Appraising Unconventional Resource Plays: Separating Reservoir Quality from Completion Effectiveness," International Petroleum Technology Conference, 2011: pp. 1-27.
Hizem et al., "SPE 116130: Dielectric Dispersion: A New Wireline Petrophysical Measurement," SPE International, 2008: pp. 1-21.
Kausik et al., "SPE 147198: Characterization of Gas Dynamics in Kerogen Nanopores by NMR," SPE International, 2011: pp. 1-16.
Meiboom et al., "Modified Spin-Echo Method for Measuring Nuclear Relaxation Times," The Review of Scientific Instruments, Aug. 1958, vol. 29(8): pp. 688-691.
Seleznev et al., "Formation Properties Derived from a Multi-Frequency Dielectric Measurement," SPWLA 47th Annual Logging Symposium, Jun. 2006: pp. 1-12.
Seleznev et al., "Applications of Dielectric Dispersion Logging to Oil-Shale Reservoirs," SPWLA 52nd Annual Logging Symposium, May 2011: pp. 1-16.
Sigal et al., "Laboratory NMR Measurements on Methane Saturated Barnett Shale Samples," Petrophysics, vol. 52(1), pp. 32-49.
Schlumberger Educational Services, "Chapter 9: Electromagnetic Propagation Logs", Schlumberger Log Interpretation Principles/Applications, Houston, TX, 1991, p. 9-1.

* cited by examiner

*Primary Examiner* — Rodney Fuller
(74) *Attorney, Agent, or Firm* — Jakub Michna

(57) ABSTRACT

Methods for the determination of the Total Gas in Place (TGiP) in gas-bearing formations are provided. Aspects of the subject disclosure also relate to the determination of the TGiP from nuclear magnetic resonance (NMR) logs alone or in combination other well logs.

23 Claims, 1 Drawing Sheet

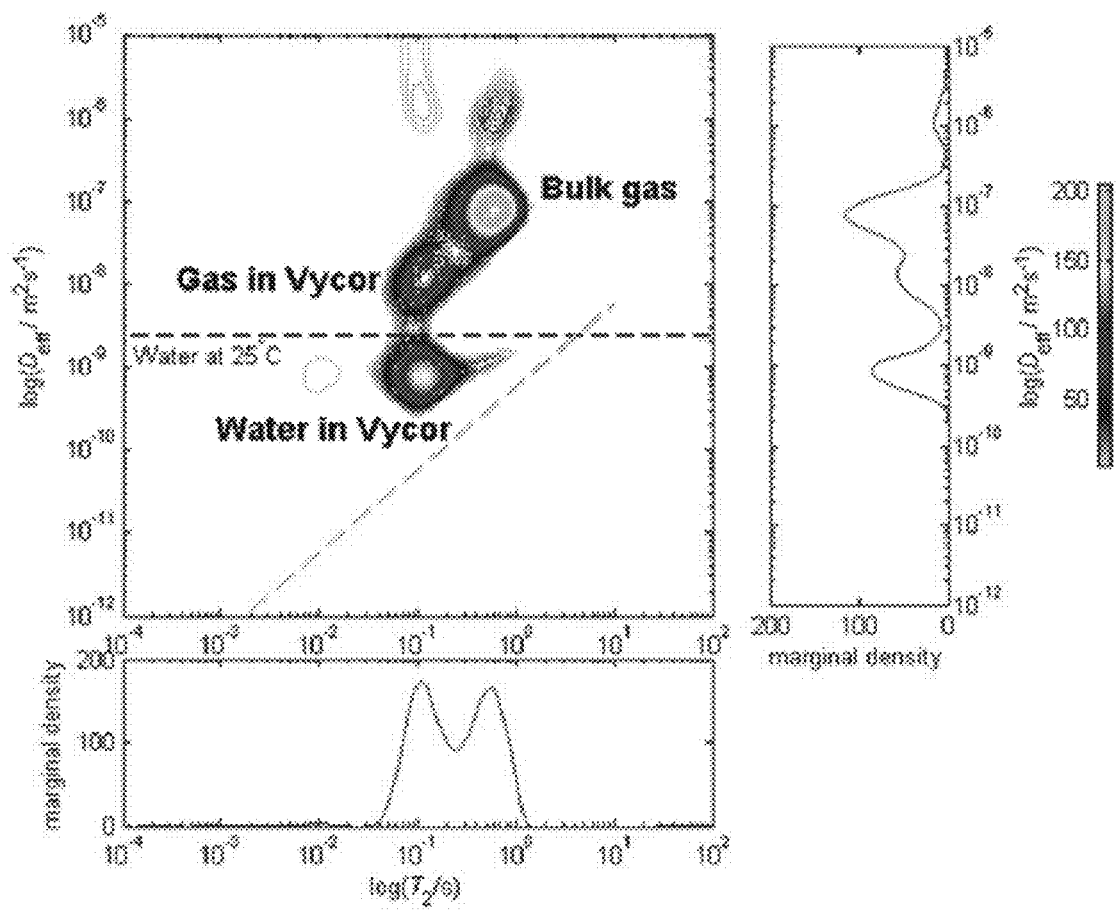
(PRIOR ART)

MULTIPHYSICS NMR LOGGING TECHNIQUES FOR THE DETERMINATION OF IN SITU TOTAL GAS IN GAS RESERVOIRS

CROSS-REFERENCE TO RELATED APPLICATION

This application claims the benefit of U.S. Provisional Patent Application Ser. No. 61/555,997 filed Nov. 4, 2011, which is incorporated herein by reference in its entirety.

BACKGROUND

When drilling a well, various logging tools and sensors are used to investigate the fluids contained within or seeping from borehole walls in order to determine if a formation contains oil or gas. One such tool is a nuclear magnetic resonance (NMR) logging tool. NMR logging tools can be used to determine properties of earth formation, such as the fractional volume of mobile fluid within the pore space, hydrogen density, diffusion, and the fractional volume of pore space (porosity).

NMR tools measure the relaxation rates of hydrogen atoms in the pore spaces of earth formations by emitting a sequence of radio-frequency pulses into a formation subject to an applied magnetic field and then monitoring the response. The amplitude of the response is measured by the NMR tool and is proportional to the mean density of hydrogen nuclei in the fluid that occupies the pore spaces in the probed volume. Because the hydrogen densities in water and in liquid hydrocarbons are known, the detected NMR signal is proportional to the volume fraction of liquid occupying the pore space.

Most NMR logging tools are tuned to detect hydrogen resonance signals (from either water or hydrocarbons), because hydrogen nuclei are the most abundant and easily detectable. Depending on factors such as the surrounding chemical environment and molecular size of the parent molecule, hydrogen nuclei exhibit different dynamic properties (e.g., diffusion rate and can tumbling/rotation rate). The different dynamic properties of these nuclei manifest themselves in different nuclear spin relaxation times that may be categorized as spin-lattice relaxation time (T1), spin-spin relaxation time (T2), and overall diffusion of the nuclei in the surrounding media (D). For example, molecules in viscous oils cannot diffuse or tumble as fast as those in light oils. As a result, hydrogen nuclei present in diffusion restricted environments (i.e., condensed or liquid phases) have shorter relative relaxation times than hydrogen nuclei in chemical environments having higher average diffusion such as gases. In a particular example, the data acquired from the NMR logging tool may provide valuable information about the molecular properties of hydrocarbons and aqueous fluids within earthen formations.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments of the present disclosure relate to methods for measuring in-situ total gas content of a subterranean formation, such as a natural gas reservoir that include: emplacing a nuclear magnetic resonance (NMR) tool into a borehole within an earthen formation; logging the borehole with the NMR tool and obtaining one or more NMR logs; separating a water-filled porosity from the one or more NMR logs obtained from the NMR tool; determining a NMR measured gas-filled porosity; calculating a total gas in place (TGiP) log of the reservoir from the NMR measured gas-filled porosity or a combination thereof In another aspect, embodiments of the present disclosure relate to methods of measuring in-situ total gas content of a natural gas reservoir including: emplacing a nuclear magnetic resonance (NMR) tool into a borehole in an earthen formation; logging the borehole with the NMR tool and obtaining one or more NMR logs; emplacing a second tool into the earthen formation and determining a second log, wherein the second log is one or more selected from a dielectric log, a resistivity log, other combinations of logs, and cuttings analysis as a function of depth; using the second log to determine a water-filled porosity; adjusting the NMR measured porosity to remove the water-filled porosity component determined from the dielectric log to determine a NMR measured gas-filled porosity; and calculating a total gas in place (TGiP) of the natural gas using the concentration of constituent gas components and the NMR measured gas-filled porosity.

In yet another aspect, embodiments of the present disclosure relate to methods of measuring total gas in place including: determining a mean number of hydrogen atoms per gas molecule; determining an NMR measured gas-filled porosity; and calculating a total volume of gas based on the mean number of hydrogen atoms per gas molecule and the NMR measured gas-filled porosity.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF DRAWINGS

FIG. 1 shows a D-$T_2$ map taken from a sample of 4 nm Vycor glass beads saturated by water and gas gas (Kausik et al., "Characterization of Gas Dynamics in Kerogen Nanopores" by NMR, SPE ATCE Denver, USA, 2011), which illustrates the separation of water and gas contributions of NMR signal in accordance with an embodiment of the present disclosure.

DETAILED DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

The following description provides exemplary embodiments only, and is not intended to limit the scope, applicability or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Also, it is noted that individual embodiments may be described as a process may be described as operations of a sequential process, many of the operations can be performed in parallel or concurrently. In addition, the order of the operations may be re-arranged. A process may be terminated when its operations are completed, but could have additional steps not discussed. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the disclosure may be implemented, at least in part, either manually or automatically. Manual or automatic implementations may be executed, or at least assisted, through the use of machines, hardware, software, firmware, middleware, microcode, hardware description languages or any combination thereof. When implemented in software, firmware, middleware or microcode, the program code or code segments to perform the necessary tasks may be stored in a machine readable medium. A processor(s) may perform the necessary tasks.

Most NMR logging tools measure the spin-lattice (longitudinal) relaxation times ($T_1$) and/or spin-spin (transverse) relaxation time ($T_2$) of hydrogen nuclei. In addition, some NMR logging tools may also provide a ratio of $T_1/T_2$ directly and/or diffusion constants (D). For example, $T_1$ relaxation may be measured using an inversion recovery or a simple spin-echo pulse sequence or any derivative thereof. In one or more embodiments, $T_2$ relaxation may be measured from a train of spin-echoes that are generated with a series of pulses such as the Carr-Purcell-Meiboom-Gill (CPMG) pulse sequence or some variant of this. The CPMG pulse sequence is known in the art and described in greater detail in Meiboom, S., Gill, D., 1958, "Modified Spin Echo Method for Measuring Nuclear Relaxation Times," Review of Scientific Instruments, 29, 688-91. The CPMG pulse sequence generates a train of spin echoes, whose amplitudes exponentially decay as a function of time. Analysis of the amplitudes of the spin echoes may then be used to obtain relaxation time $T_2$.

In embodiments of the disclosure, methods of measuring in-situ total gas content of a reservoir are disclosed. In one non-limiting example, the in-situ total gas content of a reservoir is calculated from nuclear magnetic resonance (NMR) measurements. Embodiments of the subject disclosure also relate to methods of determining the Total Gas in Place (TGiP) in earthen formations such as gas shale, from one dimensional relaxation NMR logs ($T_1$, $T_2$, $T_1/T_2$ or D) or multidimensional logs ($T_1$-$T_2$, $T_2$-D, etc.). In a gas-bearing formation, TGiP is a measure of the total amount of gas in a region of the formation, and may be a direct reflection of the net worth of a particular reservoir. Moreover, knowledge of the gas quantity as a function of depth is also useful for identification of gas bearing zones. Thus, determination of TGiP and obtaining hydrocarbon gas quantity logs may have significant commercial value, particularly in unconventional gas reservoirs such as gas shales.

In one or more embodiments, NMR measurements may be obtained from NMR tools that include wireline NMR tools, logging-while-drilling NMR tools, modular formation dynamics testers and laboratory NMR instruments.

For many formations, determination of gas volumes from NMR logs is straightforward once the number of hydrogen atoms per unit volume divided by the number of hydrogen atoms per unit volume of pure water at surface conditions, i.e., the hydrogen index (HI), is determined. For unconventional gas-bearing reservoirs such as gas shales, coalbed methane, tight sandstones, methane hydrates, and the like, quantification of the amount of gas can be problematic. In many instances the gas quantification in standard reservoirs is done using estimations based on gas pressure. However, for unconventional gas-bearing reservoirs, oils and gases are trapped in nanometer-sized pores in the formation rock. Pores present in such reservoirs may also have walls that have heterogeneous compositions that may vary from inorganic minerals to organic materials such as kerogen. In such reservoirs, gas in the proes may exist in various phases, such as an adsorbed gas on the pore walls or a free gas within the pore interiors, for example. These variations in formation composition can have unpredictable effects on the pressure-density relationships of gases and liquids present in the formation and introduce appreciable uncertainty in calculating the TGiP through the usual methodologies.

Moreover, organic matrices, such as those present in tight gas shales, are also hydrophobic and may interact through molecular-scale forces (e.g., dipolar forces, Van der Waals forces, etc.) with hydrocarbon gases present in the formation. Within organic matrices, hydrocarbon gases may also adsorb onto pore walls, decreasing the diffusion of hydrocarbon molecules and altering the response of such molecules to logging techniques. In addition to altering the diffusion of hydrocarbon molecules, adsorption of gases may cause the observed $T_1$ and $T_2$ relaxation time signal from a hydrocarbon gas to convolve with that of the water present in the formation.

Prior approaches to resolve the NMR signal contribution of hydrocarbon gases from that of formation waters include those described in U.S. Patent Pub. 2011/133859 and U.S. Pat. No. 7,755,354. However, such methods require taking multiple core samples and performing off-site laboratory tests in order to determine the water-filled porosity of a particular interval of the wellbore, which can add additional expense and time to the process of wellbore characterization. In addition, the technical difficulty of removing cores from specific depths and correlating data obtained from the cores to the corresponding NMR data can result in unacceptable error in the resulting calculation of total gas present in a given formation.

As mentioned above, in unconventional reservoirs such as gas shale, gas molecules may have a greater affinity for components of pore walls in the formation such as kerogen or other organic materials, which results in the absorption and condensation of a fraction of gas present onto the pore walls. When viewed on an NMR log output from a downhole NMR tool, the presence of an absorbed phase and a gaseous phase within the pore interior results in a non-homogenous hydrogen density throughout the formation, with the result that the net hydrogen index (HI) obtained is a weighted average of the number of proton spins in the two phases. Because the calculation of the HI represents only a weighted average, the resulting calculated TGiP of a given formation may have a greater than acceptable degree of uncertainty. Furthermore, due to the presence of unknowns such as the gas pressure differences in various organic and inorganic pores and the respective densities of the adsorbed and gaseous phases of the gas or gas mixture in the formation, it may not be possible to calculate gas quantity or TGiP reliably using conventional interpretation procedures even when the water contribution is removed.

However, in embodiments described herein, data produced from NMR tool sensors may be used to determine the density of hydrogen atoms in both the adsorbed and gaseous phases within the formation, in addition to differentiating between water and hydrocarbon gas components. Further, once the number of hydrogen atoms of the gas and the overall composition of the gas is determined, these values may be used to calculate the quantity of gas in the formation, and which may be summed over the entire log, to define the "Total gas in place" (TGiP).

Determination of Total Gas in Place

In one aspect, embodiments of the subject disclosure relate to methods for determining the TGiP for a reservoir in scf (standard cubic feet) from NMR logs, without determining secondary derived quantities such as, for example, water-filled porosity, gas-filled porosity or hydrogen index (HI), which may not be calculated directly in the presence of exchanging free and adsorbed gas.

Measurements obtained from an NMR tool (such as $T_1$, $T_2$, $T_1/T_2$ and D) are proportional to the number of nuclear spins (i.e., protons) present in a given interval of the wellbore or sample. For example, if the quantity of fluids the interval is known, then the porosity may be determined. In standard practice, the NMR tools have been calibrated to 100% porosity with water at the surface, whose hydrogen index is assigned a value of one. NMR porosity logs may therefore be obtained down hole, by comparing the measured $T_1$ or $T_2$ response for each fluid with the calibrated 100% porosity. In one or more embodiments, NMR porosity logs may be obtained by correlating a measured $T_2$ response for each fluid with the calibrated 100% porosity.

Embodiments of the present disclosure may apply to situations where the reservoir only contains water and gas as well as to situations in which some oil is present. The NMR determined porosity for a reservoir containing water and gas may be given by Eq. 1:

$$\Phi_{MR} = HI_w V_w (1 - e^{-p/T_{1w}}) + HI_g V_g (1 - e^{-p/T_{1g}}), \quad (1)$$

where $HI_w$ and $HI_g$ are the hydrogen index of the water and gas phase, $V_w$ and $V_g$ are the respective volumes of the water and gas phases, p is the wait time, $T_1$ the spin lattice relaxation time and $1 - e^{-p/T_1}$ is the insufficient polarization time. Eq. 1 can be rewritten as Eq. 2:

$$\Phi_{MR} = HI_w (1 - S_g) \phi (1 - e^{-p/T_{1w}}) + HI_g S_g \phi (1 - e^{-p/T_{1g}}), \quad (2)$$

where $S_g$ is the fraction of the pore volume filled with gas (gas saturation) and $\phi$ the is the actual porosity, i.e., the volumetric fraction of the rock that is pore space. In the case of complete polarization of the spins, the NMR measured porosity is given by Eq. 3:

$$\Phi_{MR} = HI_w (1 - S_g) \phi + HI_g S_g \phi. \quad (3)$$

If the gas and water contributions can be separated in the $T_2$ or $T_1$ dimension or by two-dimensional means (e.g., D-$T_2$, $T_1$-$T_2$), then the gas saturation factor ($S_g = 1 - S_w$) can be calculated. The apparent NMR gas-filled porosity can be expressed Eq. 4.

$$\Phi_{MR(gas)} = HI_g S_g \phi. \quad (4)$$

Therefore, knowledge of the gas phase hydrogen index (obtained from knowledge of formation temperature and pressure, and the known equation of state of natural gas) and the actual porosity (generally obtained from other well logs) connects apparent NMR gas-filled porosity with gas saturation. The hydrogen index of the bulk gas depends on the density which is a function of temperature and pressure, as show in Eq. 5:

$$HI_g = \frac{M_w}{\rho_w n_w} \frac{\rho_g n_g}{M_g} \quad (5)$$

where $\rho_w$ and $\rho_g$ are the mass densities of water and gas, $n_w$ and $n_g$ are the number of protons in each molecule of water and gas, and $M_w$ and $M_g$ are the molecular weights of water and gas. In the case of a multi-component natural gas, this analysis can be extended to give Eq. 6:

$$HI_g = \frac{M_w}{\rho_w n_w} \sum_i \alpha_i \frac{\rho_{gi} n_{gi}}{M_{gi}} \quad (6)$$

where $\alpha_i$ is the mole fraction of a gas i in the mixture. In gas reservoirs, the gas filled porosity $\Phi_{MR(gas)}$ may be determined by combining equations (4) and (6).

In the case of tight gas reservoirs such as gas shales, the majority of gaseous hydrocarbons may reside in micro- to nano-meter sized pores of an organic matrix (e.g., kerogen) or an inorganic matrix. Moreover, gaseous hydrocarbons may exist in two phases: (1) a high density phase in which gas is adsorbed on pore surfaces and (2) a lower density phase composed of free gas present in pore interiors. Here, because the hydrogen index assumes a uniform density of gas in the pore space, a measured hydrogen index value may not be representative of the actual gas component, and therefore may not be useful for accurately determining the amount of gas present in both pore spaces as well as absorbed in the pore surfaces.

In one aspect, embodiments of the subject disclosure relate to methods for obtaining the TGiP directly from the NMR logs, which may account for free gas present in pore interiors as well as absorbed on pore surfaces, without determination of the hydrogen index. Further, embodiments of the subject disclosure relate to methods for obtaining the TGiP from NMR logs where the gas contribution is separable with NMR or other techniques known to those skilled in the art, from the bound water signal.

In one or more embodiments, the total gas in place for a gas reservoir may involve determining a mean number of hydrogen atoms per gas molecule for gas in the gas reservoir; determining an NMR measured gas-filled porosity; and calculating a total volume of gas based on the mean number of hydrogen atoms per gas molecule and the NMR measured gas-filled porosity. The ability to derive the total volume of gas based on the mean number of hydrogen atoms per gas molecule and an NMR log is detailed through the below series of equations.

Many magnetic resonance borehole logging tools have complex spatial variations of sensitivity. The NMR signal of the gas phase may be given by Eq. 7:

$$V_g = \int d\vec{r} \cdot \omega(\vec{r}) \cdot M_g(\vec{r}) \cdot \left(\frac{B_1(\vec{r})}{I_1}\right), \quad (7)$$

where $\omega(\vec{r})$ is the spatially varying Larmor precession frequency, $M_g(\vec{r})$ is the spatially varying magnetic moment of the gas protons per unit formation volume and the $B_1(\vec{r})/I_1$ is the spatially varying response function of the antenna. The Larmor precession frequency is given by Eq. 8.

$$\omega(\vec{r}) = \gamma B_0(\vec{r}), \quad (8)$$

where $\gamma$ is the gyromagnetic ratio of the proton and $B_0(r)$ is the applied magnetic field. The magnetic moment per unit volume of the gas phase is given by Eq. 9:

$$M_g(\vec{r}) = \frac{\chi_g(\vec{r}) B_0(\vec{r})}{\mu_0}, \quad (9)$$

where $\mu_0$ is the magnetic permeability of free space. The Curie Law proton susceptibility of the gas in the formation, $\chi_g$ is given by Eq. 10:

$$\chi_g(\vec{r}) = \mu_0 (D_{Hg}(\vec{r})) \frac{\gamma^2 I(I+1)\hbar^2}{3kT}, \quad (10)$$

where $D_{Hg}$ is the number density of hydrogen nuclei in gas in the formation and I is the spin of the proton.

Assuming the density of hydrogen nuclei in gas is uniform over volumes small compared to the sensed volume of the logging tool but large compared to the pore sizes (a valid approximation for gas shale, in which invasion of borehole fluid is negligible), the NMR signal of the gas phase (shown in Eq. 7) can be rewritten as shown in Eq. 11:

$$V_g = D_{Hg} \int d\vec{r} \cdot \gamma B_0^2(\vec{r}) \cdot \frac{\gamma^2 I(I+1)\hbar^2}{3kT} \cdot \left(\frac{B_1(\vec{r})}{I_1}\right), \quad (11)$$

where the integral is a tool constant, determined by measuring the signal from a calibration fixture filled with water. The number density of hydrogen nuclei of the water ($D_{Hw}$) in the master calibration fixture is given by Eq. 12:

$$D_{Hw} = \frac{n_w n_A \rho_w}{M_w}, \quad (12)$$

where $n_w=2$ hydrogen atoms/molecule, which is the number of hydrogen atoms in a water molecule, $n_A=6.022 \times 10^{23}$ molecules/mole is Avogadro's Number, $M_w=18.02$ g/mole is the molecular weight of water and $\rho w$ is the density of water.

Similarly the number density of hydrogen nuclei of gas in the gas shale formation is given by Eq. 13:

$$D_{Hg} = \bar{n}_g n_A \nu \quad (13)$$

where $\bar{n}_g$ is the mean number of hydrogen atoms per gas molecule in the natural gas mixture, and $\nu$ is the number of moles of natural gas (free+adsorbed) per unit volume of gas shale formation. Connecting this notation to the standard log analysis parameter gives Eq. 14:

$$\phi_{MR}(\text{gas}) = \frac{D_{Hg}}{D_{Hw}} = \frac{M_w}{n_w \rho_w} \bar{n}_g \nu \quad (14)$$

Here, it is noted that $\phi_{MR}$(gas) is not a fraction of pore space, but simply the sum of components of the $T_2$ distribution with no hydrogen index or gas density correction of any kind Thus, the gas-filled porosity may be determined directly, potentially decreasing the need to determine the hydrogen index for the gas or water contribution, which may result in increased accuracy of the calculated TGiP by decreasing the amount of uncertainty introduced by variations in the hydrogen density that may render the hydrogen index unreliable as described above.

At standard pressure and temperature conditions, gases in a natural gas mixture obey the ideal gas law: the partial pressure of each component is proportional to the number density of that component. At chemical standard conditions (1 atmosphere pressure, 0° C. temperature) a mole of gas mixture occupies 22,414 cm³/mole. At oilfield standard conditions (1 atmosphere pressure, 60° F. temperature) a mole of gas mixture occupies 23,518 cm³/mole=0.8305 scf/mole, where scf is a cubic foot at oilfield standard conditions. Therefore, the Total Gas in Place (TGiP) in the formation is obtained by Eq. 15:

$$V_{scf} = (0.8305 \text{ scf/mole}) \cdot (10^6 \text{ cm}^3/\text{m}^3) \cdot \nu \quad (15)$$

where $V_{scf}$ is the volume (in standard cubic feet) of gas per cubic meter of formation and $\nu$ is in moles per cubic centimeter. Combining the above gives Eq. 16:

$$V_{scf} = \left(0.8305 \times 10^6 \frac{scf/\text{m}^3}{\text{mole/cm}^3}\right) \cdot \phi_{MR}(\text{gas}) \cdot \frac{n_w \rho_w}{M_w} \cdot \frac{1}{\bar{n}_g} \quad (16)$$

The gas quantity log, Eq. 16, may be integrated over depth, and the TGiP log can be determined. The advantage of using the above analysis by calibrating the NMR signal response for $D_{Hg}$ instead of porosity, is that the hydrogen index, which is not defined in gas shale reservoirs, does not enter the calculation.

While Eq. 16 relies on oilfield standard conditions, the calculation can be varied to account for changes in temperature and pressure to determine the volume occupied by a mole of gas. Further, given that $n_w$ is the number of hydrogen atoms in a water molecule, $\rho_w$ is the density of water, and $M_w$ is the molecular weight of water, all of which are known values, calculation of the volume (in standard cubic feet) of gas per cubic meter of formation only necessitates knowing $\phi_{MR}(gas)$ (i.e., the gas-filled porosity) and $n_g$ (the mean number of hydrogen atoms per gas molecule in the gas mixture).

In many natural gas reservoirs, particularly those rich in methane ("dry gas"), $n_g=4$ is accurate. Moreover, $n_g=4$ is generally the best value to use in Eq. 16 where no information about gas composition is available.

In some reservoirs, particularly those with substantial amounts of ethane, propane and butane ("wet gas"), or with substantial amounts of non-hydrocarbon gases such as carbon dioxide, knowledge of the natural gas composition may improve the accuracy of TGiP. The effective contribution of the different constituents to the NMR signal depends on their partial pressures and the number of protons in their molecular formulae through the factor $n_g$ in the equation immediately above.

Determination of Gas Composition

Knowledge of gas composition may also aid in the estimation of the economic value of the resource. Methane, generally the major constituent, has a particular market price, whereas the higher hydrocarbon compounds, e.g., ethane, pentane and butane, frequently command higher prices. Hydrogen sulfide, which is also a constituent of TGiP, has a negative market value, as it is often separated and disposed of.

In an aspect of the present disclosure, the use of downhole NMR tools may be combined with other techniques to quantify the fractional gaseous hydrocarbon components present in a gas reservoir. Methods that can provide gas composition include, for example techniques such as downhole Fluid Analysis (DFA), production data, offset wells, mud logging and NMR-based techniques.

In one or more embodiments, gases contained in wellbore fluids may be separated and identified by DFA. During DFA, a sample of gas is drawn from the earth formation using a downhole tool, where it is analyzed by various means. In embodiments in accordance with the present disclosures, DFA may be based on optical spectroscopy methods, which are capable of characterizing hydrocarbon compositions into a number of groups that include methane (C1), ethane (C2), propane to pentane (C3-C5), hexane and heavier hydrocarbons (C6+), and carbon dioxide ($CO_2$).

In other embodiments, mud logging methods may be used to characterize gaseous hydrocarbons withdrawn from the formation. In mud logging, gases from the drilling mud are measured quantitatively by gas chromatography or other means, and associated with a particular depth interval by a number of techniques know in the art. In an embodiment in accordance with the present disclosure, the mud logging method may be Fluid Logging and Analysis in Real Time (FLAIR) offered by Geoservices, a division of Schlumberger. FLAIR provides a quantitative analysis of C1-C5 and qualitative information on the C6-C8 components and light aromatics.

In one or more embodiments, production data from the well of interest or nearby offset wells can be used to determine average gas compositions. Such techniques may data lack depth specificity, but can be useful for horizontal wells where gas compositions may be substantially uniform over the length of the well.

In one or more embodiments of the present disclosure, the mean number of hydrogen atoms per gas molecule in the gas mixture, $\bar{n}_g$, may be calculated by determining the partial pressures of each of the constitutive components of the natural gas mixture. The partial pressures of methane, ethane, propane and non-hydrocarbon gases (e.g., nitrogen, carbon dioxide, etc.) are $p_1$, $p_2$, $p_3$ and $p_0$, respectively. The mean number of hydrogen atoms per gas molecule in the gas mixture can then be represented by Eq. 17:

$$\bar{n}_g = 0 \cdot \frac{p_0}{p} + 4\frac{p_1}{p} + 6\frac{p_2}{p} + 8\frac{p_3}{p} + \ldots \tag{17}$$

where $p_0$ is the total partial pressure of the non-hydrocarbon gases and the total pressure of the gas mixture is represented Eq. 18:

$$p = \sum_i p_i \tag{18}$$

In other embodiments, the gas composition may be determined using data obtained using NMR-based methods such as those described in U.S. Pat. No. 6,859,032, assigned to the same assignee and incorporated herein by reference.

Resolving Water and Gas Contributions in the NMR Log

Embodiments of this disclosure may further relate to methods to resolve gas and water signals in data generated from NMR logging tools so that the gas-filled porosity may be determined. Water also contributes to the total magnetic resonance signal, and may be removed prior to gas analysis. By separating the gas and water contributions of the NMR signal, the water-filled porosity may be determined using a cutoff time or other means so that the water-filled porosity may be separated out from the total porosity to determine the gas-filled porosity. In that case the NMR measured gas-filled porosity may be given by Eq. 19:

$$\phi_{MR}(gas) = \phi_{MR} - \phi_{MR}(water) \tag{19}$$

where $\phi_{MR}$ is the NMR-determined porosity (e.g., TCMR porosity) and $\phi_{MR}(water)$ is the NMR determined water-filled porosity.

In one or more embodiments, the quantification of TGiP from the gas contribution may be achieved using a hydrogen index independent analysis subsequent to the resolution of the water and gas contributions. Techniques used to resolve water-filled porosity and gas-filled porosity in accordance with embodiments disclosed herein include techniques such as NMR well log relaxation analysis, NMR well log two dimensional relaxation analysis, NMR well log diffusion-relaxation analysis, resistivity well log analysis, dielectric well log analysis, cuttings analysis, and the like. Some methods to carry out the resolution of the water and gas contributions to NMR-determined porosity are also discussed in other works of the inventors (see Kausik et al., U.S. Provisional Patent Application Ser. No. 61/521,860, which is herein incorporated by reference in its entirety and Kausik et al., "Characterization of Gas Dynamics in Kerogen Nanopores" by NMR, SPE ATCE Denver, USA, 2011).

In one or more embodiments of the present disclosure, the relaxation time $T_2$ may be used to separate the NMR signal and isolate the contributions from water and gas components. For example, in magnetic resonance $T_2$ logs, water and gas signals from gas shale could overlap. This happens in spite of the fact that irreducible water magnetic relaxation time peaks at 1 ms and gas magnetic relaxation time peaks at 10 ms. Downhole environments also pose challenges because of the low signal-to-noise ratio due to low porosity of gas shale reservoirs (See Kausik et al., "Characterization of Gas Dynamics in Kerogen Nanopores" by NMR, SPE ATCE Denver, USA, 2011).

In some embodiments, two dimensional NMR D-$T_2$ measurements may be applied for resolution of the water and gas signals, especially in situations where there is an overlap in the relaxation dimension. In one non-limiting example, D-$T_2$ experiments on Vycor porous glass (4 nm narrow pore size distribution) is shown in FIG. 1. In this example, the gas and water $T_2$ distributions are inseparable in the relaxation dimension, but may be resolved in the diffusion dimension. Both water and gas have lower diffusion coefficients compared to their respective bulk values due to restricted diffusion and both are separable in the diffusion dimension (See Kausik et al., "Characterization of Gas Dynamics in Kerogen Nanopores" by NMR, SPE ATCE Denver, USA, 2011 and Kausik et al., U.S. Provisional Patent Application Ser. No. 61/521, 860)). The oil, if present, would also be differentiated from the other contributions by falling on the alkane line. The water and gas contributions are separated in the diffusion dimension even though they overlap in the relaxation dimension, exhibiting the potential of 2-D NMR D-$T_2$ measurements for such applications.

Two dimensional NMR $T_1$-$T_2$ correlation experiments can also be carried out for the separation of the irreducible water and confined gas components. This is based on the premise that the $T_1/T_2$ ratio of the irreducible water is different from that of the confined gas.

In other embodiments, resistivity measurements, and logs thereof, may be used to determine the water-filled porosity $\phi_{res}(water)$ of subsurface rock formations. A number of resistivity models (models described in Cipolla, Lewis, Maxwell, and Mack, "Appraising Unconventional Resource Plays," International Petroleum Technology Conference IPTC-146677 (2011), for example) based on V-Shale (resistivity models) or Cation exchange (conductivity models) like the Modified Simandoux model have been applied on unconventional logs. Thus, the gas-filled porosity may be determined using $\phi_{res}(water)$ to correct for the water contribution of the NMR measured porosity using Eq. 20.

$$\phi_{MR}(gas) = \phi_{MR} - \phi_{res}(water) \quad (20)$$

In yet other embodiments, dielectric scanning methods may be used to correct for the water-filled porosity in unconventional reservoirs such as oil shales. Dielectric scanning methods have been employed to determine water saturation in the presence of clays, various other minerals and kerogen. For example, methods such as those described in Seleznev et al., "Applications of Dielectric Dispersion Logging to Oil Shale Reservoirs," SPWLA 52$^{nd}$ Annual Logging Symposium, Paper G, 2011 may be used to determine water-filled porosity.

In dielectric scanning techniques, a tool is emplaced in the wellbore containing, for example, a multispacing antenna array pad. As the electromagnetic waves travel from the transmitters to the receivers, changes occur in amplitude and phase that are directly related to the dielectric permittivity and conductivity of the formation. Because there is a large contrast between the permittivity of water and that of oil and of rock, the tool makes a direct measurement of the water volume that is independent of the water salinity. Inorganic minerals, kerogen, and gas have low permittivity relative to that of water, see Table 1 below. (See Seleznev, N et al., 2006. Formation Properties Derived from a Multi-Frequency Dielectric Measurement, SPWLA 47th Annual Logging Symposium, Paper VVV and Seleznev, N et al., 2011. Applications of Dielectric Dispersion Logging to Oil Shale Reservoirs, SPWLA 52nd Annual Logging Symposium, Paper G and *Schlumberger Log Interpretation Principles/Applications*, 1989).

TABLE 1

Permittivity of various formation components.

| Component | Permittivity | Reference |
|---|---|---|
| Sandstone | 4.65 | (1) |
| Limestone | 7.5-9.2 | (1) |
| Clay | 5.64 | (2) |
| Kerogen | 3.23 | (2) |
| Oil | 2.0-2.4 | (1) |
| Gas | 1.0 | (1) |

Dielectric techniques operate on the basis that matrix constituents and hydrocarbons are substantially more dielectric and appear to be part of the grain space, while water is easily detected because of its higher relative permittivity. While the presence of pyrite can be a confounding factor, because of its high relative permittivity, elemental capture spectroscopy may be used to obtain satisfactory values of its concentration in the formation when the presence of pyrite is suspected. Following the determination of the water-filled porosity, gas-filled porosity can then be determined with minimum ambiguity using Eq. 21:

$$\phi_{MR}(gas) = \phi_{MR} - \phi_{diel}(water) \quad (21)$$

where $\phi$MR is a total magnetic resonance porosity (e.g., TCMR) and $\phi$diel(water) is the water-filled porosity as determined by a dielectric logging tool.

In yet other embodiments, drill cuttings may be used to directly calculate the water-filled porosity. The drill cuttings carried up from the well by the drilling fluid may be analyzed at the well site using various techniques. The determined water-filled porosity can then be used in combination with the NMR log response to directly provide gas filled porosity from which the TGiP can be calculated using the above described methodology.

It is also envisioned that methods described herein may also be used for other unconventional reservoirs such as gas shale, tight gas, etc. and conventional gas reservoirs to obtain a TGiP well log for a wellbore in an earthen formation. Moreover, using methods described herein, TGiP may be obtained using an NMR log and one or more instrument logs and/or information obtained from drill cuttings as a function of depth. Additionally, in some embodiments, measurement and analysis of the total gas content of a formation may be done on site without the need for acquiring core samples or performing laboratory-based experiments.

As disclosed above, methods to determine TGiP may also describe how the presence of a complex composition of gases and hydrocarbons present in the formation can be taken into account when determining a total volume of gas. Further, by determining the partial pressure of each component gas and the mean number of hydrogen atoms per gas molecule, the accuracy of the calculation of total volume of gas can be improved further. In some embodiments, this information may then be used to convert directly the NMR log into a volume of gas in standard cubic feet.

In one or more embodiments, the TGiP may be measured using a continuous logging method. For example, first an NMR logging tool may be lowered into the well and operate to execute the appropriate NMR pulse sequences to measure NMR response of the reservoir fluids at multiple depths of investigation (DOI) and acquires the data continuously as the tool moves through the rock formation. The data for different DOI at the same well location (depth) is then analyzed to extract the $T_2$ log, for example, of that location. The logging data is analyzed to obtain TGiP for the entire interval of the formation.

In one or more embodiments, the TGiP may be measured using a stationary logging method. For example, first an NMR logging tool may be lowered into the well to a specified depth and operate to execute NMR pulse sequences to measure NMR response of the reservoir fluids at multiple DOIs for that well depth. The data obtained from the different DOIs may be analyzed to extract the $T_2$ log, for example, of the formation at this depth. The data and the interpretation of wettability may be transmitted to surface. If required, the tool may be moved to a different depth and perform the NMR measurements at this different depth to obtain measurements at this different depth.

Although only a few example embodiments have been described in detail above, those skilled in the art will readily appreciate that many modifications are possible in the example embodiments without materially departing from the present disclosure. Accordingly, all such modifications are intended to be included within the scope of this disclosure as defined in the following claims. Moreover, embodiments disclosed herein may be practiced in the absence of any element which is not specifically disclosed.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The invention claimed is:

1. A method of measuring total gas in place for a subterranean formation traversed by a borehole, comprising:
    emplacing a nuclear magnetic resonance (NMR) tool into the borehole;
    logging the borehole with the NMR tool to obtain an NMR log;
    determining a NMR signal corresponding to gas using the NMR log;
    determining a value corresponding to a number of hydrogen nuclei within the formation using the NMR signal corresponding to gas; and
    calculating a total gas in place (TGiP) log of the formation using the value corresponding to the number of hydrogen nuclei.

2. The method of claim 1, wherein the NMR tool comprises at least one of a wireline NMR tool, a logging-while-drilling NMR tool, a modular formation dynamics tester, and a laboratory NMR instrument.

3. The method of claim 1, further comprising:
    emplacing a second tool into the formation and determining a second log, wherein determining the NMR signal corresponding to gas further comprises determining a NMR signal corresponding to water using the second log and separating the NMR signal corresponding to water from the NMR signal corresponding to gas.

4. The method of claim 3, wherein the second log comprises a NMR log, a dielectric log, a resistivity log, cuttings analysis as a function of depth, or a combination thereof.

5. The method of claim 1,
    wherein the value corresponding to the number of hydrogen nuclei is a value corresponding to a number of methane hydrogen nuclei, and
    wherein the value corresponding to the number of methane hydrogen nuclei is determined using a gas composition.

6. The method of claim 5, further comprising:
    determining the gas composition using downhole fluid analysis, mud logging, production data from the borehole, production data from a nearby well, or a combination thereof.

7. The method of claim 6, wherein determining the gas composition comprises determining partial pressures of constituents of the gas composition.

8. The method of claim 1, wherein the value corresponding to the number of hydrogen nuclei within the formation is a number of moles of hydrogen nuclei within the formation.

9. The method of claim 8, wherein the following relationship is used to determine the number of moles of hydrogen nuclei within the formation:

$$v = \phi_{MR(gas)} \cdot \frac{n_w \rho_w}{M_W} \cdot \frac{1}{\bar{n}_g}$$

wherein $v$ is the number of moles of hydrogen nuclei within the formation, $\rho_w$ is the mass density of water, $n_w$ is the number of hydrogen nuclei in each molecule of water, $M_w$ is the molecular weight of water, $\phi_{MR}(gas)$ is the NMR signal corresponding to gas, and $\bar{n}_g$ is the mean number of hydrogen nuclei per gas molecule in a gas mixture.

10. The method of claim 8, wherein the number of moles of hydrogen nuclei within the formation is a number of moles of hydrogen nuclei per unit volume of gas.

11. The method of claim 1, further comprising:
    separating a NMR signal corresponding to water from the NMR log, wherein the separating is performed using NMR well log relaxation analysis, NMR well log dimensional relaxation analysis, NMR well log diffusion-relaxation analysis, resistivity well log analysis, dielectric well log analysis, cuttings analysis, or a combination thereof; and
    after separating the NMR signal corresponding to water from the NMR log, determining the NMR signal corresponding to gas using the NMR log.

12. The method of claim 11, further comprising using one or more of D, $T_1$, $T_2$, and any ratio thereof to separate the NMR signal corresponding to water from the NMR log.

13. The method of claim 1, wherein the method is performed without using a hydrogen index.

14. The method of claim 1, wherein the method is performed without using a density for the gas.

15. A method of measuring total gas in place for a subterranean formation, comprising:
    emplacing a nuclear magnetic resonance (NMR) tool into the borehole;
    logging the borehole with the NMR tool to obtain an NMR log;
    determining a mean number of hydrogen nuclei per gas molecule in the formation;
    determining a NMR signal corresponding to gas within the formation using the NMR log; and
    calculating a total volume of gas using the mean number of hydrogen nuclei per gas molecule and the NMR signal corresponding to gas within the formation.

16. The method of claim 15, wherein calculating the total volume of gas comprises calculating a volume of gas per unit volume and calculating the total volume by integration of the NMR log for an entire depth of the gas reservoir.

17. The method of claim 15, wherein determining the mean number of hydrogen nuclei comprises determining partial pressures of constituents of the gas within the formation.

18. The method of claim 15, wherein determining the NMR signal corresponding to gas further comprises determining the NMR signal corresponding to water and separating the NMR signal corresponding to water from the NMR signal corresponding to gas.

19. The method of claim 18, wherein the separating is performed using NMR well log relaxation analysis, NMR well log two dimensional relaxation analysis, NMR well log diffusion-relaxation analysis, resistivity well log analysis, dielectric well log analysis, cuttings analysis, or a combination thereof.

20. The method of claim 15, wherein the determining the mean number of hydrogen nuclei per gas molecule for the gas comprises:
   determining gas composition information for the gas in the formation; and
   calculating the mean number of hydrogen nuclei per gas molecule for the gas.

21. The method of claim 15, wherein the determining the mean number of hydrogen nuclei per gas molecule for the gas comprises estimating the mean number.

22. The method of claim 15, wherein the method is performed without using a hydrogen index.

23. The method of claim 15, wherein the method is performed without using a density for the gas.

* * * * *